United States Patent [19]
Krespan et al.

[11] Patent Number: 5,908,966
[45] Date of Patent: *Jun. 1, 1999

[54] THERMAL PROCESS FOR THE PREPARATION OF A TELOMERIC ALKYL IODIDE

[75] Inventors: Carl George Krespan, Wilmington; Viacheslav A. Petrov, Hockessin, both of Del.

[73] Assignee: E. I. du Pont de Nemours and Company, Wilmington, Del.

[21] Appl. No.: 08/987,632

[22] Filed: Dec. 9, 1997

Related U.S. Application Data

[60] Provisional application No. 60/062,098, Oct. 14, 1997.
[51] Int. Cl.$^6$ ................................................... C07C 21/18
[52] U.S. Cl. ................................................................ 570/139
[58] Field of Search ............................................. 570/139

[56] References Cited

U.S. PATENT DOCUMENTS

| | | | |
|---|---|---|---|
| 3,132,185 | 5/1964 | Parsons | 260/653 |
| 3,234,294 | 2/1966 | Parsons | 260/653.1 |
| 3,404,189 | 10/1968 | Blochl | 260/653.1 |
| 4,067,916 | 1/1978 | Jaeger | 260/653.1 |
| 5,268,516 | 12/1993 | Bertocchio et al. | 570/139 |
| 5,574,193 | 11/1996 | Krespan et al. | 570/172 |

FOREIGN PATENT DOCUMENTS

| | | | | |
|---|---|---|---|---|
| 1096687 | 12/1967 | United Kingdom | ............ | C07C 19/08 |
| 1218528 | 1/1971 | United Kingdom | ............ | C07C 19/08 |
| 1535408 | 12/1978 | United Kingdom | ............ | C07C 17/28 |

OTHER PUBLICATIONS

W–Y. Chen et al., *J. Fluor. Chem.* 36(4), 483–489, 1987.

*Primary Examiner*—Zinna Northington Davis

[57] ABSTRACT

Disclosed herein is a telomerization process for preparing fluorinated alkyl iodide telomers, comprising telomerizing a starting polyfluoroalkyl iodide with a terminally unsaturated perfluoro olefin or monochlorofluoro olefin.

10 Claims, No Drawings

THERMAL PROCESS FOR THE PREPARATION OF A TELOMERIC ALKYL IODIDE

This application claims the priority benefit of U.S. Provisional application Ser. No. 60/062,098, filed Oct. 14, 1997.

FIELD OF INVENTION

This invention relates to the thermal initiation of a telomerization process to prepare low molecular weight oligomers of fluorinated iodides. These low molecular weight oligomers are useful in synthesis processes as intermediates to surfactants.

BACKGROUND OF THE INVENTION

Telomeric polyfluoroalkyl iodides are commercial products widely used for the preparation of a variety of valuable polyfluorinated compounds. Various processes are known in the art for preparing polyfluoroalkyl iodides based on the telomerization of lower perfluoroolefins (e.g., TFE, tetrafluoroethylene) with fluoroalkyl iodides. A detailed description of the telomerization process is set forth in U.S. Pat. Nos. 3,234,294 and 3,132,185, which are incorporated herein by reference.

The telomerization process typically takes place in the presence of an initiator. Some processes are initiated by peroxy compounds (Ger. Pat. No. DE 2542496; Mar. 31, 1977); some by metals (J. Fluor. Chem. 36(4), 483–489, 1987) or salts of some metals in combination with hydroxyalkylamines (U.S. Pat. No. 4,067,916, Jan. 10, 1978) or initiated by a mixture of $IF_5/SbF_5$ (U.S. Pat. No. 3,234,294, Feb. 8, 1966).

It is known in the art that thermal reaction of polyfluoroalkyl iodides $R_fI$ with TFE leads to formation of a mixture of telomeric alkyl iodides $R_f(CF_2CF_2)_nI$ (Telomer A). Bloch (Brit. Pat. No. 1,096,687, 1968; U.S. Pat. No. 3,404,189; 1968; Brit. Pat. No. 1,218,528; 1971) prepared several fluorinated alkyl telomers (for instance, $C_6F_{13}I$ from $C_4F_9I$ and TFE) using a high molar ratio of $R_fI$/TFE, at least greater than 2:1, resulting in low conversion of TFE (10–30%).

A need exists for a telomerization process that does not use added initiators but does result in formation of low molecular weight telomers with a narrow distribution range, a high conversion of reactants but still generates high productivity. The telomers produced herein are useful as intermediates to surfactants and oil repellents.

SUMMARY OF THE INVENTION

Disclosed herein is a process for preparing fluorinated alkyl iodide telomers comprising contacting an optionally substituted polyfluoralkyl mono-iodide or di-iodide, linear or branched, optionally containing chlorine and/or bromine and/or in-chain ether oxygen or a functional group with a terminally unsaturated perfluoroolefin or monochloroperfluoroolefin, at a temperature of about 300° C. to about 400° C. wherein the ratio of the polyfluoroalkyl iodide to terminally unsaturated olefin is about 1.1–1.9 to 1.

The process also concerns an embodiment wherein the polyfluoroalkyl iodide has the general formula $XCF_2CFYI$, wherein X is F, Cl, Br, $R_f$, or $OR_f$ where $R_f$ is polyfluoroalkyl or a perfluoroalkyl group of up to 12 carbon atoms, optionally containing ether oxygen and/or I, $-SO_2F$, or $-C(O)OCH_3$, and Y is F, Cl or $CF_3$.

DETAILED DESCRIPTION OF THE INVENTION

By "telomerization process" herein is meant a catalytic chemical reaction in which one or more molecules of a polymerizable substance (called the taxogen) combine with the fragments of another molecule (called the telogen). An example of a telomerization process described herein is the reaction of an polyfluoroalkyl iodide (telogen) with a fluorinated olefin such as TFE (taxogen) shown by the following equation:

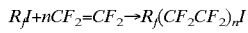

$$R_fI + nCF_2=CF_2 \rightarrow R_f(CF_2CF_2)_nI$$

wherein n is any number, preferably 1 to 10 and $R_f$ is selected from the group consisting of polyfluoroalkyl or a perfluoroalkyl group of up to 12 carbon atoms, optionally containing ether oxygen and/or I, $-SO_2F$, or $-C(O)OCH_3$.

The usual product of the telomerization process described herein is a mixture of polyfluoroalkyl iodides having a broad molecular weight distribution rather than a single product. Various methods are used to control the molecular weight distribution of product, including use of effective chain transfer agents (Hazeldine, J. Chem. Soc. 3761 (1953)), and by performing the telomerization process rapidly in the gas phase as described in U.S. Pat. No. 3,404,189, which is incorporated herein by reference.

It has been found that by decreasing the molar ratio in the feed of polyfluoroalkyl iodide to tetrafluoroethylene ($R_fI$/TFE) to 1.1–1.9 to 1, a substantially complete conversion of TFE (in excess of 90%) is achieved, under the temperature conditions taught herein, along with the production of a mixture of telomers having a narrow distribution and low molecular weight. The reaction temperature for this process is about 300° C. to 400° C., preferably 320° C. to 370° C., most preferably 330° C. to 350° C. Comparable conversions of $R_fI$ is 5–50% where the ratio of $R_fI$ is not controlled as described herein. Under ideal conditions the product is free of any by-products and the process has high productivity. Despite the problems known to be associated with handling TFE at high temperatures, operation at the high ratios of TFE delineated above can be carried out without the danger of uncontrolled reaction or explosion. (See U.S. Pat. No. 3,404,189 which mentions the danger of explosion with similar reactants under atmospheric pressure conditions.) "Polyfluoroalkyl iodides" ($R_fI$) useful herein include the mono or diiodides and can be linear or branched, optionally containing chlorine and/or bromine and/or in-chain ether oxygen. Preferred iodides are represented by the general formula $XCF_2CFYI$, wherein X is F, Cl, Br, $R_f$, or $OR_f$ where $R_f$ is polyfluoroalkyl or a perfluoroalkyl group of up to 12 carbon atoms, linear or branched, optionally containing ether oxygen and/or a functional group such as I, $-SO_2F$, or $-C(O)OCH_3$, and Y is F, Cl or $CF_3$. More preferred perfluoralkyl iodides are linear. These include, but are not limited to, $CF_3CF_2I$, $CF_3CFClI$, $ClCF_2CF_2I$, $ClCF_2CFClI$, $CF_3CF_2CF_2CF_2I$, $CF_3CF_2CF_2I$, $(CF_3)_2CFI$, $ICF_2CF_2CF_2CF_2I$ and $CF_3OCF_2CF_2I$. Most preferred are perfluoroethyl iodide ($CF_3CF_2I$) and perfluoro-n-butyl iodide ($CF_3CF_2CF_2CF_2I$).

Terminally unsaturated perfluoro or monochloroperfluoroolefins for use in the process include but are not limited to $CF_2=CF_2$, $CF_2=CFCl$, and $CF_2=CFCF_3$. Preferred are terminally unsaturated perfluoroolefins. Most preferred is tetrafluoroethylene ($CF_2=CF_2$).

The ratio of polyfluoroalkyl iodide to tetrafluoroethylene ($R_fI$/TFE) is about 1.1:1 to about 1.9 to 1. A slight excess of $R_fI$ is used to lessen the explosive potential of the mixture.

The process can be performed at pressures from ambient pressure to about 250 psig (1.8 MPa). Preferred pressures are 30–150 psig. Pressures above 300 psig (2.2 MPa) are generally avoided because TFE liquidifies and is difficult to handle. The process can also be carried out under inert gas which allows for the use of higher pressures. All pressures mentioned are gauge pressures.

Residence times in the reactor is a factor in the distribution of product telomers, with longer residence time resulting in broader distributions. The instant process is run with a residence time from about one second to ten minutes, with about one second to five minutes being preferred, about one to about sixty second more preferred and about three to about thirty seconds being most preferred.

EXAMPLES

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

EXAMPLES 1–11

The reactions were carried out in the gas phase with premixtures of excess $R_fI$ with TFE in a flow system containing either a Hastelloy U-tube (residence time 5 sec.) or a coil (residence time 15 sec) reactor. All reactions were carried out inside a closed barricade. All pressures listed are gauge pressures (psig).

by an ISCO pump set at pressure of 100–110 psi. Before the reaction the whole system was purged with $N_2$ and kept under pressure of $N_2$ (100 psi). The polyfluoroalkyl iodide was loaded as a liquid in the barrel of the ISCO pump (precooled in the case of perfluoroethyl iodide (PFEI)), and the nitrogen was pushed out to leave only iodide inside of the pump. The barricade was closed and starting from this point all manipulations were carried out from outside of the barricade. To prevent the polymerization of TFE a 5 mL portion of iodide was loaded into hot reactor in the beginning and TFE feed was started immediately. In all runs the rate of alkyl iodide was kept constant (2 mL/min.). The rate of TFE was varied from 0.123 L/min. up to 0.18 L/min.

At the end of the reaction the TFE flow was cut off first, then the system was purged by $N_2$ to remove all material from the reactor. The barricade was opened and cooled reaction mixture was transferred into a glass flask. In reactions of PFEI, excess of it was distilled out on low temperature distillation column and the residue, containing some PFEI (usually 10–30%) was analyzed by GC. The product was identified by GC, $^{19}F$ NMR and by comparison with authentic samples. Samples from $C_4F_9I$/TFE runs were analyzed without removing starting iodide. Reaction was run on scales from 50 g to 200 g of starting iodide. The conditions and data on distribution of telomers for reactions of TFE with PFEI and $C_4F_9I$ are given in Table 1.

TABLE 1

| Run No. | $R_fI$ | T(°C.) | Ratio[a] | Res. Time[b] (s) | % Conv. $R_fI$ (TFE) | $n^e$ = 1 | 2 | 3 | 4 | 5 | 6 | 7 | 8 | >8 |
|---|---|---|---|---|---|---|---|---|---|---|---|---|---|---|
| Comparative Example 1 | $C_2F_5I$ | 320 | 2.96 | 15 | — | 50 | 21.8 | 12.7 | 6.8 | 4.0 | 2.5 | 1.7 | 1.1 | 1 |
| Comparative Example 2 | $C_2F_5I$ | 330 | 2.96 | 15 | — | 60.5 | 20.5 | 11 | 4.5 | 2.0 | 1.0 | 0.5 | — | |
| Comparative Example 3 | $C_2F_5I$ | 340 | 2.96 | 15 | 12 | 58.8 | 20.6 | 11.8 | 4.8 | 2.1 | 0.8 | 0.4 | — | |
| Comparative Example 4 | $C_2F_5I$ | 350 | 2.96 | 15 | 9 | 60.8 | 21.8 | 11.7 | 3.8 | 1.4 | 0.6 | — | — | |
| Comparative Example 5 | $C_2F_5I$ | 350 | 2.29 | 5 | — | 60.0 | 22.0 | 10.5 | 3.5 | 4 (n > 4) | | | | |
| Comparative Example 6[f] | $C_2F_5I$ | 350–370[c] | 2.03 | 5 | 17 | 98 (n = 1–4) | | | | | | | | |
| Comparative Example 7 | $C_2F_5I$ | 330[c,d] | 2.03 | 5 | 25 | 55.0 | 23.0 | 11.5 | 4.8 | 5 (n > 4) | | | | |
| Comparative Example 8[f] | $C_2F_5I$ | 350–370[c] | 2.03 | 5 | 11 | 57.0 | 22.0 | 13.0 | 5.0 | 2.0 | 2 (n > 5) | | | |
| Comparative Example 9 | $C_2F_5I$ | 330[c,d] | 2.03 | 5 | 17.5 (92) | 58.3 | 23.3 | 12.8 | 5.7 | 1.2 | — | — | | |
| Example 10[g] | $C_4F_9I$ | 330[c,d] | 1.54 | 5 | 33 (100) | 58.6 | 20.4 | 11.6 | 3.1 | n > 4 (6.3) | | | | |
| Example 11 | $C_4F_9I$ | 330[c,d] | 1.54 | 5 | 24 (100) | 61.5 | 19.5 | 10 | 4 | n > 4 (6) | | | | |

[a]Molar ratio $R_fI$/TFE: 2.96 -PFEI 2 mL/min.; TFE 0.123 L/min.; 2.03 PFEI - 2 mL/min; TFE 0.16 L/min.; 1.54: $C_4F_9I$ - 2 mL/min., TFE 0.18 L/min.
[b]Calculated, 15 s for ¼ inch coil Hastelloy tube, length 77 inches; 5 s for ¼ inch Hastelloy U-tube, 25 inches
[c]Exothermic reaction
[d]Temperature was maintained at 330–350° C.
[e]Weight % (GC data)
[f]The product contained significant amounts (>5%) of perfluoroalkane coupling products
[g]Crude reaction mixture (wgt. %): $C_2F_5I$ 12.7, $C_4F_9I$ 56.1, higher telomers –31.2

The reaction zone was kept under pressure by means of three grove valves (on TFE and alkyl iodide lines and one installed after the reactor), the reactor was heated by a sand bath, and the temperatures were controlled by two thermocouples inside of the reactor and one in the sand bath. The TFE from a special reservoir (pressure=300 psi) was introduced into the system through a pressure reducing grove valve set at 210 psi, and the flow was measured by a mass flow meter. The alkyl iodide was introduced into the reactor

What is claimed is:

1. A process for preparing fluorinated alkyl iodide telomers comprising contacting an optionally substituted polyfluoralkyl mono-iodide or di-iodide, linear or branched, optionally containing chlorine and/or bromine and/or in-chain ether oxygen or a functional group with a terminally unsaturated perfluoroolefin or monochloroperfluoroolefin, at a temperature of about 300°

C. to about 400° C. wherein the ratio of the polyfluoroalkyl iodide to terminally unsaturated olefin is about 1.1–1.9 to 1.

2. The process of claim 1 wherein the polyfluoroalkyl iodide has the formula $XCF_2CFYI$, wherein X is F, Cl, Br, $R_f$, or $OR_f$ where $R_f$ is polyfluoroalkyl or a perfluoroalkyl group of up to 12 carbon atoms, optionally containing ether oxygen and/or I, $-SO_2F$, or $-C(O)OCH_3$, and Y is F, Cl or $CF_3$.

3. The process of claim 2 wherein the polyfluoroalkyl iodide is linear.

4. The process of claim 3 wherein the polyfluoroalkyl iodide is selected from the group consisting of $CF_3CF_2I$, $CF_3CFClI$, $ClCF_2CF_2I$, $ClCF_2CFClI$, $CF_3CF_2CF_2CF_2I$, $CF_3CF_2CF_2I$, $(CF_3)_2CFI$, $ICF_2CF_2CF_2CF_2I$ $CF_3OCF_2CF_2I$.

5. The process of claim 4 wherein the polyfluoroalkyl iodide is selected from the group consisting of $CF_3CF_2I$, $CF_3CF_2CF_2I$, and $CF_3CF_2CF_2CF_2I$.

6. The process of claim 1 wherein the perfluoroolefin or chlorofluoroolefins are selected from the group consisting of $CF_2=CF_2$, $CF_2=CFCl$, and $CF_2=CFCF_3$.

7. The process of claim 6 wherein the perfluoroolefin or chlorofluoroolefin is $CF_2=CF_2$.

8. The process of claim 3 wherein the polyfluoroalkyl iodides are selected from the group consisting of linear perfluoroalkyl iodides and linear perfluoroalkyl diiodides.

9. The process of Claim 3 wherein the polyfluoroalkyl iodide is perfluoroethyl iodide and the perfluoroolefin is tetrafluoroethylene.

10. The process of claim 4 wherein the polyfluoroalkyl iodide is selected from the group consisting of $CF_3CF_2I$, $CF_3CF_2CF_2CF_2I$, $CF_3CF_2CF_2I$, $(CF_3)_2CFI$, $ICF_2CF_2CF_2CF_2I$ and $CF_3OCF_2CF_2I$.

* * * * *